(12) United States Patent
Ruiz

(10) Patent No.: US 10,413,393 B2
(45) Date of Patent: Sep. 17, 2019

(54) FILLER MANIPULATOR APPARATUS

(71) Applicant: Melanie Ruiz, Fair Oaks, TX (US)

(72) Inventor: Melanie Ruiz, Fair Oaks, TX (US)

( * ) Notice: Subject to any disclaimer, the term of this patent is extended or adjusted under 35 U.S.C. 154(b) by 0 days.

(21) Appl. No.: 14/353,243

(22) PCT Filed: Sep. 30, 2013

(86) PCT No.: PCT/US2013/062568
§ 371 (c)(1),
(2) Date: Apr. 21, 2014

(87) PCT Pub. No.: WO2014/171968
PCT Pub. Date: Oct. 23, 2014

(65) Prior Publication Data
US 2016/0278907 A1   Sep. 29, 2016

Related U.S. Application Data

(60) Provisional application No. 61/811,849, filed on Apr. 15, 2013.

(51) Int. Cl.
*A61B 17/00* (2006.01)
*A61F 2/00* (2006.01)
*A61B 17/34* (2006.01)

(52) U.S. Cl.
CPC ........ *A61F 2/0059* (2013.01); *A61B 17/3468* (2013.01); *A61B 2017/00792* (2013.01); *A61B 2017/00946* (2013.01)

(58) Field of Classification Search
CPC .......... A61B 17/00491; A61B 17/3468; A61B 2017/00792; A61F 2/0059

USPC ........................................................ 606/214
See application file for complete search history.

(56) References Cited

U.S. PATENT DOCUMENTS

| | | |
|---|---|---|
| 5,286,193 A | 2/1994 | Roane |
| 2002/0120283 A1 | 8/2002 | Holmes |
| 2005/0131393 A1* | 6/2005 | Chu ................. A61B 17/00234 606/1 |
| 2008/0103452 A1* | 5/2008 | Voegele ........... A61B 17/00491 604/187 |
| 2009/0208893 A1* | 8/2009 | Bertram-Jakobsen ... A61C 5/00 433/29 |
| 2013/0108352 A1* | 5/2013 | Ruiz, Sr. ................ B65D 35/36 401/132 |

OTHER PUBLICATIONS

Patent Cooperation Treaty, International Search Report, dated Jan. 2, 2014, Korean Intellectual Property Office.

\* cited by examiner

*Primary Examiner* — Melanie R Tyson
(74) *Attorney, Agent, or Firm* — Hulsey P.C.

(57) ABSTRACT

Disclosed a filler manipulator apparatus which includes a first elongated section, a second elongated section, wherein the second elongated section may have at least one bend, more than one bend, or a ball and socket joint in the structure of the second elongated section. The embodiment further includes a tip extension connected to a portion of the second elongated section, wherein the tip extension is made to receive a filler effector associated by a protuberance and a groove, more than one protuberance, or a snap ring. The filler effector rotates about the tip extension and is used to manipulate filler located on or in a body and may be enveloped in a polymer.

19 Claims, 9 Drawing Sheets

FILLER MANIPULATOR APPARATUS

CROSS-REFERENCE TO RELATED APPLICATIONS

This application claims the priority of PCT Application No. PCT/US2013/062568, filed on Sep. 30, 2013.

FIELD OF THE INVENTION

The present disclosure relates to a system of adjustable and detachable handpieces for use in cosmetic surgery filler manipulation.

BACKGROUND OF THE INVENTION

One of the most established markets in today's medical field is the cosmetic surgery market. Every year, billions of dollars are spent by consumers on an assortment of body augmentations. This surgical rejuvenation fad first became popular back in the late 1990s. It was at this time that many biocompatible materials became widely available to surgeons for use in body augmentation procedures.

A very popular biocompatible material that has been used in the past is collagen. Collagen requires an allergy test by a patient since it is extracted from bovine hides. It may last anywhere from four to twelve weeks because it is also absorbed in to the body.

Autologen is an example of another biocompatible material that has been used in the past. It is an injectable dermal material made from a patient's own skin. There is not a risk of allergic reaction with autologen, however, the results stemming from surgery using autologen are very temporary because of the fact that the body quickly absorbs the material. Dermalogen is a filler taken from a patient's skin. Through a laboratory process, this filler is made into a high concentration collagen that can be injected. It has been studied that dermalogen may last somewhat longer than collagen. Another example of a filler is Alloderm® (a registered trademark of LifeCell Corporation). Alloderm® is a donor tissue taken from cadavers that is denatured, purified, and treated in order to remove viable cells that could pass along disease. It is a popular filler for lip injections. Under a local anesthesia, Alloderm® is placed into the mucosa, or body, of the lips in small rolls to make them larger. The filler may also be placed into the vermilion, the pink area of the lip, to provide definition and a sharper border. All of the fillers listed so far have been used in the past. More efficient fillers are used today.

The fillers used today may typically be divided into two categories: hyaluronic acids and "other fillers". Hyaluronic acids can further be broken down into two categories: regular lasting and long lasting. The regular lasting category includes fillers such as Restylane, Juvederm Ultra, and Prevelle.

Restylane® (a registered trademark of Q-Med) is a filler recommended for patients with mild to moderate facial wrinkles and for patients who want softer lips. It is preferred that Restylane® be used on first time and/or younger patients. Restylane® lasts four to six months and is soft and easier to use than most other fillers. A second very popular regular filler is Juvederm Ultra® (a registered trademark of Allergan, Inc.). Juvederm Ultra® is similar to Restylane® in softness and is also preferred in younger patients and/or patients with mild to moderate wrinkles. Prevelle® (a registered trademark of Mentor Worldwide LLC) is a third very popular regular filler. It is similar to Restylane® and Juvederm Ultra® but is softer. Prevelle® is used for mild wrinkles and is good for the lips, but does not last as long as Restylane® or Juvederm Ultra®.

The group of longer lasting hyaluronic acids include Juvederm Ultra Plus® (a registered trademark of Allergan, Inc.) and Perlane® (a registered trademark of HA North American Sales AB). Juvederm Ultra Plus® lasts for eight to nine months or longer and is good for moderate to severe wrinkles. It is also thicker than Juvederm Ultra® and therefore requires more massage to assure there is no lumpiness in the treated area. Perlane® may last eight to nine months or longer and is good for moderate to severe wrinkles. It is also a thicker filler and therefore requires more massage around the treated area to assure there is no lumpiness.

The fillers that make up the "other fillers" category includes Radiesse® (a registered trademark of Merz Aesthetics), Sculptra® (a registered trademark of Valeant Pharmaceuticals International, Inc.), Artefill® (a registered trademark of Suneva Medical, Inc.), and fat. Radiesse® is a synthetic, laboratory produced solution containing calcium hydroxylapatite suspended in a gel. It is a biocompatible material that has been safely used in medicine for years. Studies have shown that Radiesse® can last between three and five years when used for bodily enhancement. The filler lasts nine months to a year and is very good for the treatment of severe wrinkles or areas that need a "firmer" filler to correct a defect such as an ear lobe, the nose, filling depressed scars, and the forehead. A massage of the treatment area is necessary after surgery in order to prevent nodules. Sculptra®, or poly-L-lactic acid) promotes collagen synthesis or remodeling. It has been used worldwide since 1999. Artefill® comprises polymethylmethacrylate (PMMA) microspheres and purified bovine collagen. Polymethylmethacrylate is a plastic compound that requires a patient to undergo allergy testing to make sure that they are not allergic to the compound. It has been used in medicine previously as a glue compound for hip prostheses. Claims have been made that Artefill® could last five years, but testing is still being done in order to prove that claim. Fat is a natural, non allergenic alternative to dermal fillers. It contains growth factors and stem cells that not only fill, but synthesize collagen and skin cells so that a patient's skin over the filled area even looks better. Fat may last two to four years or longer.

Another example of a biocompatible material is Gore-Tex® (a registered trademark of W.L. Gore & Associates) implants. Gore-Tex® is also referred to as EPTFE, or expanded polytetrafluoroethylene, in the medical field and Advanta™, Ultrasoft™, and SoftForm™ in the marketplace. The EPTFE that comprises Gore-Tex is delivered to surgeons in strips that are either $\frac{1}{16}$ inch or $\frac{3}{16}$ inch diameter tubes.

However, after injecting (or placing) the filler material in the patient, the filler must be shaped or formed to achieve the desired effect. Currently, there is not a well established tool for aiding in the manipulation of filler during cosmetic surgery. Doctors and clinicians today may use something similar to a Q-tip® (a registered trademark of Unilever). There are a number of different cosmetic surgeries that would benefit from a filler manipulator.

Periorbital surgery is one example of a surgery that would benefit from a filler manipulator. The periorbital is the area situated around the orbit of the eye. Periorbital soft tissues are easily contused and produce marked inflammatory responses to trauma. Because the cotton swab requires significant pressure and repeated strokes (e.g. passes over the skin to form the filler injected (or placed) below the skin) to properly form the filler, extensive contusions and inflammation are the norm.

The zygomatic arch is the arch formed by the processes of the zygomatic and temporal bones. It is the bone that forms the hard part of the cheek and the lower, lateral portion of the rim of the orbit. Surgery for this part of the body requires filler manipulation at a precise angle. Again, the use of cotton swabs to form filler in this area is inherently difficult and very time consuming because of the relatively sharp angles desired of the final product.

Rhinoplasty means nose molding or nose forming. It refers to a procedure in plastic surgery in which the structure of the nose is changed. These alterations may be made by adding or removing bone or cartilage, grafting tissue from another part of the body, or implanting synthetic material to alter the shape of the nose. If breathing is impaired due to the form of the nose or injury, using a non-surgical approach will help alleviate these symptoms only on a temporary basis (acts like a splint). A non-surgical approach, such as applying an implant/filler, is most often used for correction of a crooked nose, malformation at birth, or a deformity caused by an injury or cancer. The quality of the skin plays a major role in the outcome of both approaches.

Mandible is the medical term for the lower jaw, specifically, the horseshoe-shaped bone forming the lower jaw. It consists of a central portion, which forms the chin and supports the lower teeth, and perpendicular portions, or rami, which point upward from the back of the chin on either side and articulate with the temporal bones. Tense/rigid ligaments, tendons, and muscles pull the jaw bone long enough to cause displacements of the jaw and jaw pain. Having surgery or a non-surgical approach with a neurotoxin or filler will provide the patient relief in pain. The non-surgical approaches are great options for those who do not want surgery or those who are not candidates for surgery.

Large cavities and regions of the body can require a substantial amount of replacement filler. Parts of the body such as the buttocks, arm, leg, and abdominal region fall under this category. These areas may require a large amount of filler and therefore a lot of surgical attention.

Genitalia enhancements are another popular surgical procedure. This type of procedure involves the addition of very sensitive filler to the vaginal and penile regions. These areas also may require a lot of surgical attention.

Accordingly, a need exists for cosmetic surgery tools that allow a patient a better outcome, less chance of an infection, and a quicker recovery time.

BRIEF SUMMARY OF THE INVENTION

The disclosure at hand provides a filler manipulator apparatus for use in cosmetic surgery. One embodiment of the filler manipulator apparatus comprises a first elongated section. The first elongated section may comprise an exterior high friction layer and/or grooves. The filler manipulator apparatus further comprises a second elongated section connected to a portion of the first elongated section, wherein the second elongated section may comprise at least one bend, more than one bend, or a ball and socket joint in the structure of the second elongated section. A tip extension is connected to a portion of the second elongated section, wherein the tip extension is made to receive a filler effector associated by a protuberance and a groove, more than one protuberance, or a snap ring. The filler effector may be enveloped in a polymer.

Accordingly, it is a principal object of the current disclosure to overcome the disadvantages of tools used for filler manipulation during cosmetic surgery by allowing a patient a better outcome, a more precise look, less trauma and injury to the tissue, less chance of infection, a faster recovery and outcome and allowing a doctor reduced fatigue and reduced pain (e.g., if a doctor suffers from carpal tunnel or arthritis) due to the adaptability of the filler manipulation apparatus.

These and other aspects of the disclosed subject matter, as well as additional novel features, will be apparent from the description provided herein. Provided, however, any particular embodiment need not contain all of the aspects and aspects from one embodiment may be implemented in another embodiment and remain within the scope of this disclosure. Furthermore, any particular aspect may be removed from one or more embodiments and remain within the scope of this disclosure. The intent of this summary is not to be a comprehensive description of the subject matter, but rather to provide a short overview of some of the subject matter's functionality. Other systems, methods, features and advantages here provided will become apparent to one with skill in the art upon examination of the following FIGURES and detailed description. It is intended that all such additional systems, methods, features and advantages that are included within this description, be within the scope of any claims filed later.

BRIEF DESCRIPTION OF THE DRAWINGS

The novel features believed characteristic of the disclosed subject matter will be set forth in the claims and any claims that are filed later. The disclosed subject matter itself, however, as well as a preferred mode of use, further objectives, and advantages thereof, will best be understood by reference to the following detailed description of an illustrative embodiment when read in conjunction with the accompanying drawings, wherein:

DETAILED DESCRIPTION OF ILLUSTRATIVE EMBODIMENTS

Reference now should be made to the drawings, in which the same reference numbers are used throughout the different figures to designate the same components.

It will be understood that, although the terms first, second, third, etc. may be used herein to describe various elements, these elements should not be limited by these terms. These terms are only used to distinguish one element from another element. Thus, a first element discussed below could be termed a second element without departing from the teachings of the present disclosure.

The terminology used herein is for the purpose of describing particular embodiments only and is not intended to be limiting. As used herein, the singular forms "a", "an", and "the" are intended to include the plural forms as well, unless the context clearly indicates otherwise. It will be further understood that the terms "comprises" and/or "comprising" or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The use of any and all examples, or exemplary language (e.g., "such as"), is intended merely to better illustrate the disclosure and does not pose a limitation on the scope of the disclosure unless otherwise claimed. No language in the specification should be construed as indicating any non-claimed element as essential to the practice of the disclosure as used herein.

Figure 1A:
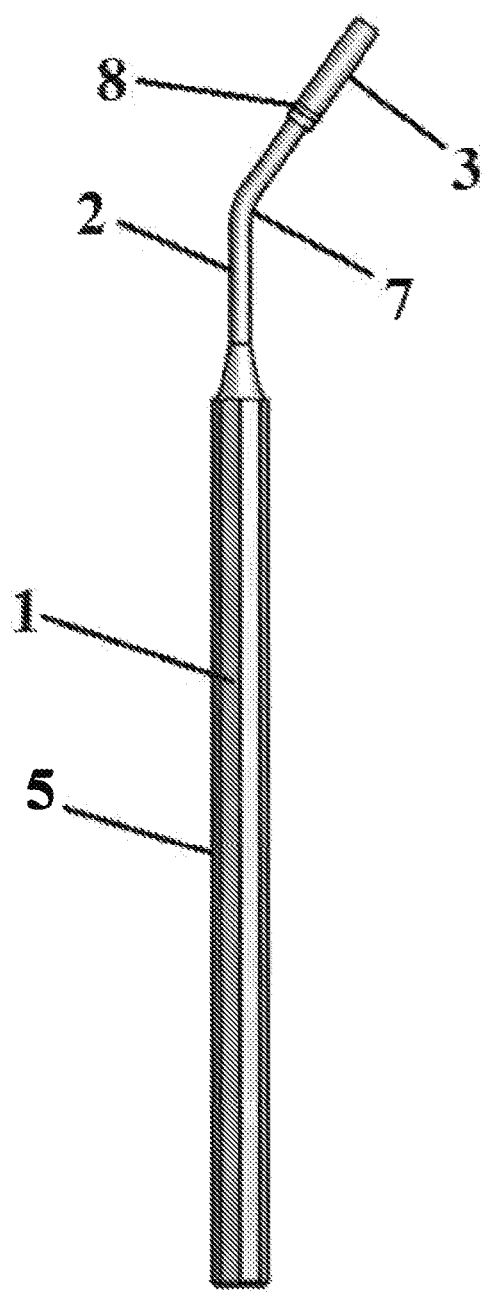
FIG. 1A depicts a side view of a filler manipulator apparatus with a protuberance according to an embodiment of the current disclosure.

FIG. 1A depicts an embodiment of a filler manipulator apparatus. The first elongated section 1 is the longest section and its longitudinal body comprises eight sides (not including the base/bases of the first elongated section). The first elongated section 1 serves the purpose of being a handle for the filler manipulator apparatus. The second elongated section 2 is connected to a portion of the first elongated section 1. The second elongated section 2 comprises at least one bend 7. The at least one bend 7 allows for certain angles of application of the filler effector 4 when the filler effector 4 is connected to a tip extension 3. In some instances of manipulation of filler, it will be advantageous to utilize the specific angle at which the second elongated section 2 is bent. The tip extension 3 is connected to a portion of the second elongated section 2. A protuberance 8 runs around the perimeter of the tip extension 3. When a filler effector 4 (see FIGS. 5A-5G) is placed on the tip extension 3, a protuberance found on the inside circumference of the filler effector 4 will fit over the protuberance 8 of the tip extension 3 and create an interlocking mechanism. This connection between the tip extension 3 and the filler effector 4 will keep the filler effector 4 securely fastened to the tip extension 3. With the filler effector 4 securely fastened to the tip extension 3, the filler manipulator apparatus is used to manipulate filler on or in a body. It is noteworthy that the filler effector 4 is allowed to rotate about the tip extension 3 even after the filler effector 4 is securely fastened to the tip extension 3.

In another embodiment, the longitudinal body of the first elongated section 1 may comprise more or less than eight sides (not including the base/bases of the first elongated section). The body may therefore take the shape of a cylinder, a prism, a nonagonal prism, etc. This may also include any array of abstract sides that do not constitute a formal shape.

In another embodiment, the second elongated section 4 may be longer in length than the first elongated section 1 and the tip extension 3.

In another embodiment, the second elongated section 2 may be longer in length than the first elongated section 1 and the tip extension 3.

In another embodiment, the tip extension 3 may be longer in length than the first elongated section 1 and the second elongated section 2.

In another embodiment, the filler manipulator apparatus comprises a high friction layer 5 cloaking the first elongated section 1. The high friction layer 5 allows for a decreased likelihood that the filler manipulator apparatus will slip out of a user's hand when the filler manipulator device is being used.

Figure 1B:
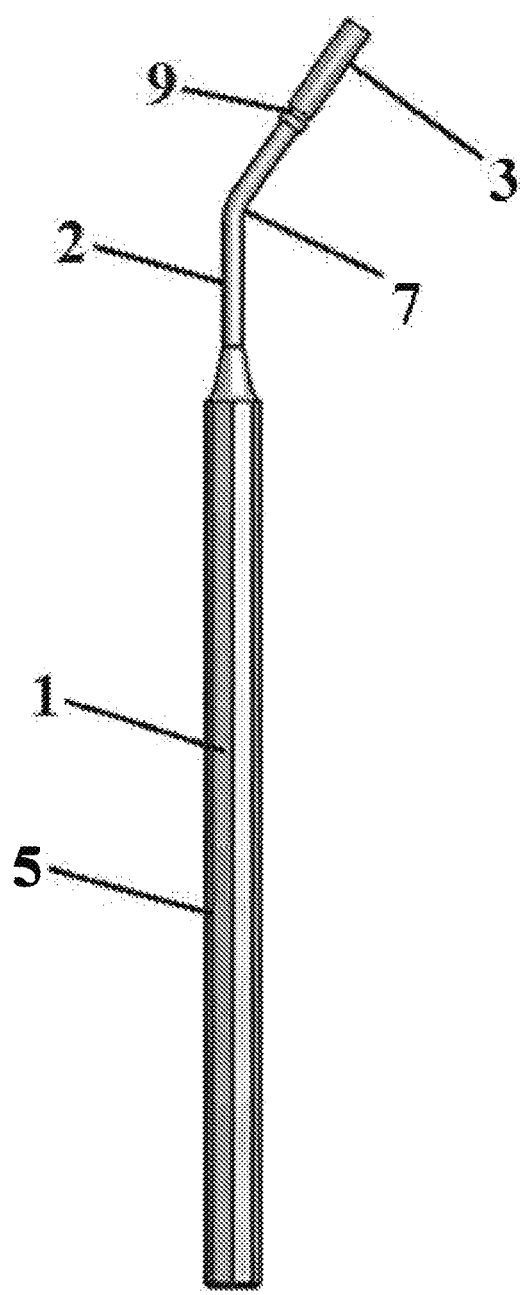
FIG. 1B depicts a side view of a filler manipulator apparatus with a circular groove according to an embodiment of the current disclosure.

FIG. 1B depicts an embodiment of a filler manipulator apparatus. The first elongated section 1 is the longest section and its longitudinal body comprises eight sides (not including the base/bases of the first elongated section). The first elongated section 1 serves the purpose of being a handle for the filler manipulator apparatus. The second elongated section 2 is connected to a portion of the first elongated section 1. The second elongated section 2 comprises at least one bend 7. The at least one bend 7 allows for certain angles of application of the filler effector 4 when the filler effector 4 is connected to a tip extension 3. In some instances of manipulation of filler, it will be advantageous to utilize the specific angle at which the second elongated section 2 is bent. The tip extension 3 is connected to a portion of the second elongated section 2. A circular groove 9 runs around the perimeter of the tip extension 3. When a filler effector 4 is placed on the tip extension 3, a protuberance found on the inside circumference of the filler effector 4 will fit snugly into the circular groove 9 of the tip extension 3. This connection between the tip extension 3 and the filler effector 4 will keep the filler effector 4 securely fastened to the tip extension 3. With the filler effector 4 securely fastened to the tip extension 3, the filler manipulator apparatus is used to manipulate filler on or in a body. It is noteworthy that the filler effector 4 is allowed to rotate about the tip extension 3 even after the filler effector 4 is securely fastened to the tip extension 3. Again, the filler effector 4 is allowed to rotate about the tip extension 3 even after the filler effector 4 is securely fastened to the tip extension 3. Additionally, all of the embodiments listed with reference to FIG. 1A apply equally to FIG. 1B.

Figure 1C:
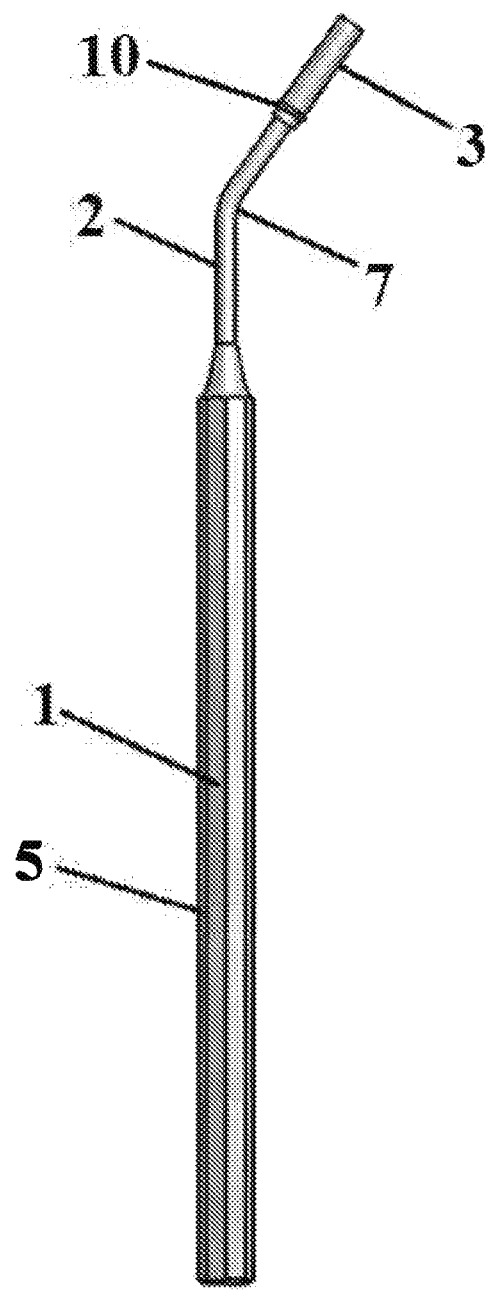
FIG. 1C depicts a side view of a filler manipulator apparatus with a snap ring according to an embodiment of the current disclosure.

FIG. 1C depicts an embodiment of a filler manipulator apparatus. The first elongated section 1 is the longest section and its longitudinal body comprises eight sides (not including the base/bases of the first elongated section). The first elongated section 1 serves the purpose of being a handle for the filler manipulator apparatus. The second elongated section 3 is connected to a portion of the first elongated section 1. The second elongated section 2 comprises at least one bend 7. The at least one bend 7 allows for certain angles of application of the filler effector 4 when the filler effector 4 is connected to a tip extension 3. In some instances of manipulation of filler, it will be advantageous to utilize the specific angle at which the second elongated section 2 is bent. The tip extension 3 is connected to a portion of the second elongated section 2. A protuberance 8 runs around the perimeter of the tip extension 3. When a filler effector 4 is placed on the tip extension 3, a snap ring 10 found on a portion of the tip extension 3 will fit over a portion of the filler effector 4 and secure the filler effector 4 to the tip extension 3. With the filler effector 4 securely fastened to the tip extension 3, the filler manipulator apparatus is used to manipulate filler on or in a body. It is noteworthy that the filler effector 4 is allowed to rotate about the tip extension 3 even after the filler effector 4 is securely fastened to the tip extension 3. Again, the filler effector 4 is allowed to rotate about the tip extension 3 even after the filler effector 4 is securely fastened to the tip extension 3. Additionally, all of the embodiments listed with reference to FIGS. 1A and 1B apply equally to FIG. 1C.

Figure 2:
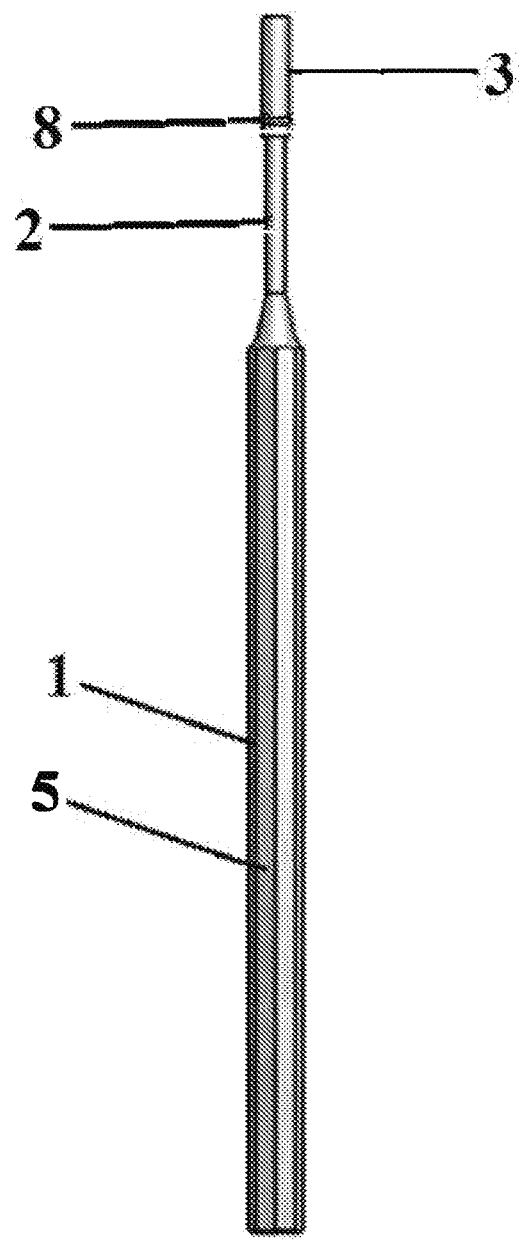
FIG. 2 depicts a side view of a filler manipulator apparatus with a straight second elongated section according to an embodiment of the current disclosure.

FIG. 2 depicts an embodiment of a filler manipulator apparatus. The first elongated section 1 is the longest section and its longitudinal body comprises eight sides (not including the base/bases of the first elongated section). The first elongated section 1 serves the purpose of being a handle for the filler manipulator apparatus. The second elongated section 2 is connected to a portion of the first elongated section 1. The second elongated section 2 is straight, which allows for this particular embodiment to be used in different situations as opposed to embodiments with at least one bend in the second elongated section 2. In some instances of application of filler effector, it will be advantageous to utilize the specific angle at which the second elongated section 2 is bent. The tip extension 3 is connected to a portion of the second elongated section 2. A protuberance 8 runs around the perimeter of the tip extension 3. When a filler effector 4 is placed on the tip extension 3, a protuberance found on the inside circumference of the filler effector 4 will fit over the protuberance 8 of the tip extension 3 and create an interlocking mechanism. This connection between the tip extension 3 and the filler effector 4 will keep the filler effector 4 securely fastened to the tip extension 3. With the filler effector 4 securely fastened to the tip extension 3, the filler manipulator apparatus is used to manipulate filler on or in a body. It is noteworthy that the filler effector 4 is allowed to rotate about the tip extension 3 even after the filler effector 4 is securely fastened to the tip extension 3. Again, the filler effector 4 is allowed to rotate about the tip extension 3 even after the filler effector 4 is securely fastened to the tip extension 3. Additionally, all of the embodiments listed with reference to FIGS. 1A, 1B, and 1C apply equally to FIG. 2.

Figure 3:
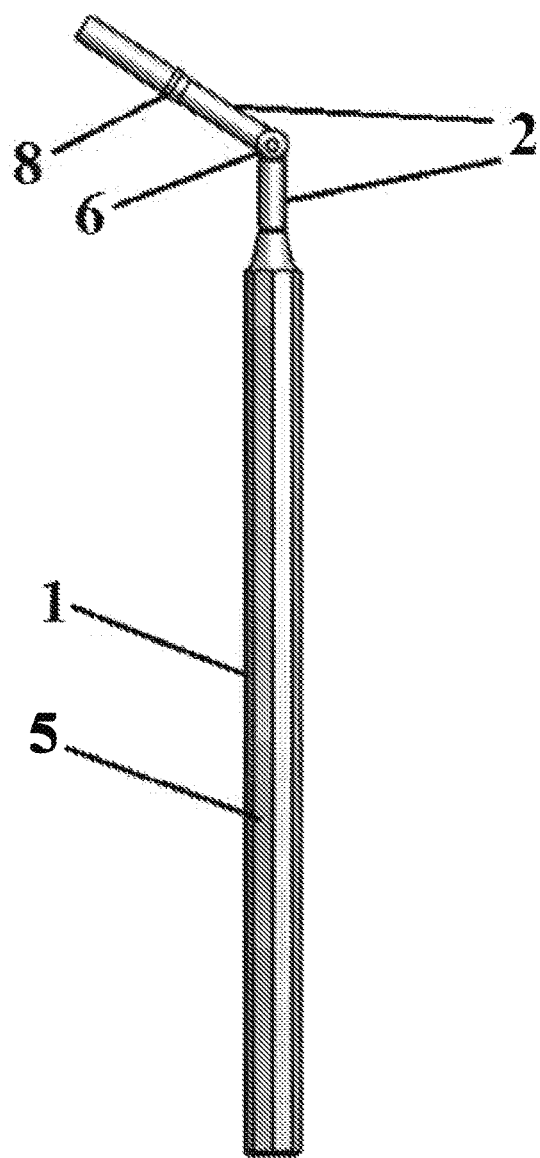
FIG. 3 depicts a side view of a filler manipulator apparatus with a ball and socket joint according to an embodiment of the current disclosure.

FIG. 3 depicts an embodiment of a filler manipulator apparatus. The first elongated section 1 is the longest section and its longitudinal body comprises eight sides (not including the base/bases of the first elongated section). The first elongated section 1 serves the purpose of being a handle for the filler manipulator apparatus. The second elongated section 2 is connected to a portion of the first elongated section 1. An adjustable attachment 6 exists at a portion of the second elongated section. The adjustable attachment 6 serves the purpose of changing the angle of application of the filler effector 4 when the filler effector 4 is connected to a tip extension 3. Some examples of an adjustable attachment 6 that may be used include a ball and socket joint and a screw joint; the embodiments of a filler manipulator apparatus are not limited to these examples and may use other suitable adjustable attachments 6. The tip extension 3 is connected to a portion of the second elongated section 2. A protuberance 8 runs around the perimeter of the tip extension 3. When a filler effector 4 is placed on the tip extension 3, a protuberance found on the inside circumference of the filler effector 4 will fit over the protuberance 8 of the tip extension 3 and create an interlocking mechanism. This connection between the tip extension 3 and the filler effector 4 will keep the filler effector 4 securely fastened to the tip extension 3. With the filler effector 4 securely fastened to the tip extension 3, the filler manipulator apparatus is used to manipulate filler on or in a body. It is noteworthy that the filler effector 4 is allowed to rotate about the tip extension 3 even after the filler effector 4 is securely fastened to the tip extension 3. Again, the filler effector 4 is allowed to rotate about the tip extension 3 even after the filler effector 4 is securely fastened to the tip extension 3. Additionally, all of the embodiments listed with reference to FIGS. 1A, 1B, 1C, and 2 apply equally to FIG. 3.

In another embodiment, the adjustable attachment 6 may be located on any part of the filler manipulator apparatus in order that a first portion of the filler manipulator apparatus may be adjustably attached to a second portion of the filler manipulator apparatus.

Figure 4:
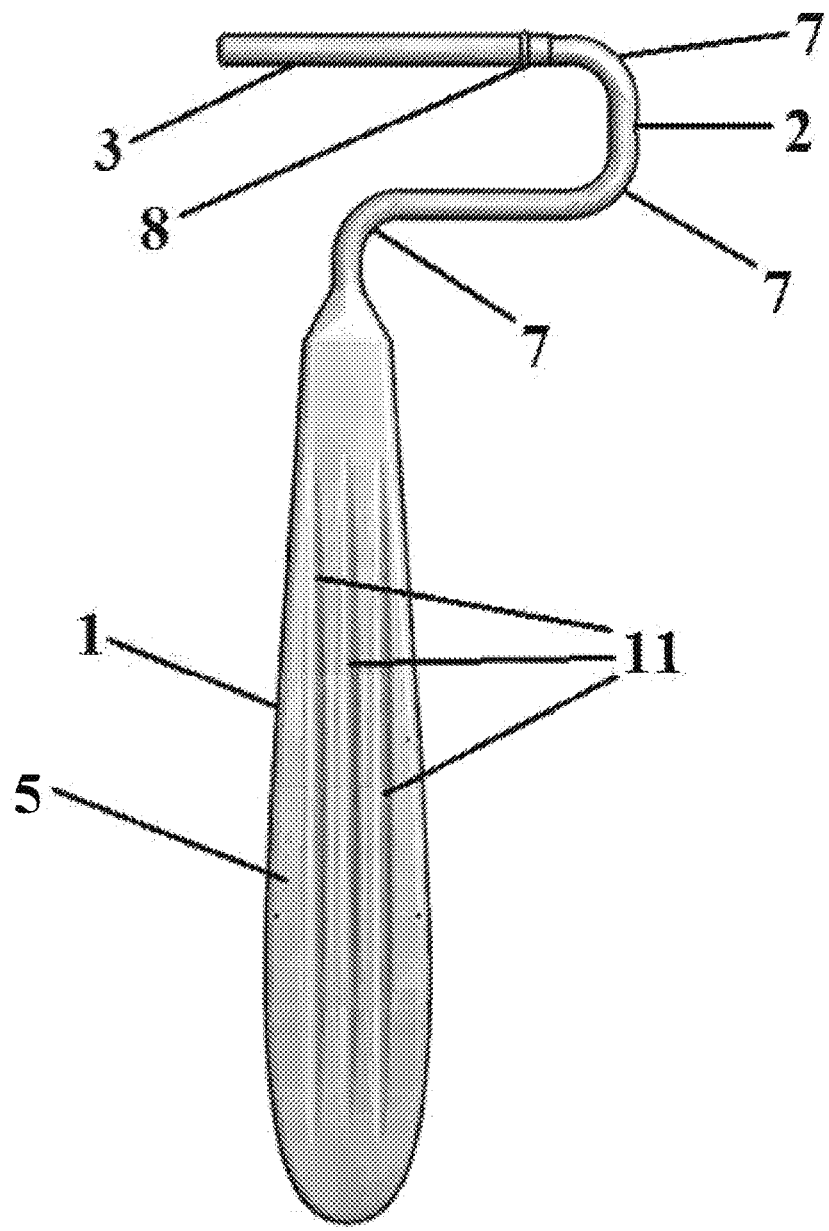
FIG. 4 depicts a side view of a filler manipulator apparatus with more than one bend in the second elongated section according to an embodiment of the current disclosure.

FIG. 4 depicts an embodiment of a filler manipulator apparatus. The first elongated section 1 is the longest section and its longitudinal body comprises a truncated ovoid shape. The first elongated section 1 serves the purpose of being a handle for the filler manipulator apparatus. The second elongated section 2 is connected to a portion of the first elongated section 1. The second elongated section 2 comprises more than one bend 7. The more than one bend 7 allows for the filler effector 4 to be applied to hard to reach areas of a body when the filler effector 4 is connected to a tip extension 3. In some instances of manipulation of filler, it will be advantageous to utilize the specific angles at which the second elongated section 2 is bent. The tip extension 3 is connected to a portion of the second elongated section 2. A protuberance 8 runs around the perimeter of the tip extension 3. When a filler effector 4 is placed on the tip extension 3, a protuberance found on the inside circumference of the filler effector 4 will fit over the protuberance 8 of the tip extension 3 and create an interlocking mechanism. This connection between the tip extension 3 and the filler effector 4 will keep the filler effector 4 securely fastened to the tip extension 3. With the filler effector 4 securely fastened to the tip extension 3, the filler manipulator apparatus is used to manipulate filler on or in a body. It is noteworthy that the filler effector 4 is allowed to rotate about the tip extension 3 even after the filler effector 4 is securely fastened to the tip extension 3. Again, the filler effector 4 is allowed to rotate about the tip extension 3 even after the filler effector 4 is securely fastened to the tip extension 3. Additionally, all of the embodiments listed with reference to FIGS. 1A, 1B, 1C, 2, and 3 apply equally to FIG. 4.

In another embodiment, the first elongated section 1 includes grooves 11. The grooves 11 allow for a proper and comfortable grip when the filler manipulator apparatus is being utilized. The grooves 11 may exist on a covering on the first elongated section 1 or on the actual first elongated section 11.

In another embodiment, the filler manipulator apparatus used for filler manipulation (minus the filler effector 4) may be fabricated from a material selected from the group of polymer, composite, metal, metal alloy, and ceramic.

In another embodiment, a filler effector 4 may be connected to a filler manipulator apparatus by a connection mechanism selected from the group of a circular groove 9 on the tip extension 3 with a protuberance 8 on the filler effector 4, a snap ring 10 encompassing the tip extension 3 and the filler effector 4, and a protuberance 8 on the tip extension 3 with a protuberance 8 on the filler effector. These connections may be utilized in any embodiment of the filler manipulator apparatus.

Figure 5A:
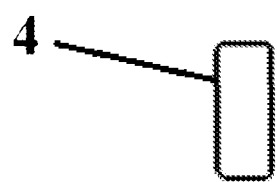
FIG. 5A depicts a side view of a cylindrical filler effector according to an embodiment of the current disclosure.

FIG. 5A depicts an embodiment of a filler effector 4. The filler effector 4 is cylindrical in appearance and comprises a hollow interior. The interior of the filler effector 4 is hollow to the point where it will comfortably slide onto a tip extension 3 of any embodiment of a filler manipulator apparatus and not drop free off of the tip extension 3. It is noteworthy that the filler effector 4 is allowed to rotate about the tip extension 3 even after the filler effector 4 is securely fastened to the tip extension 3. It is preferred that this embodiment of a filler effector 4 is utilized in the manipulation of the periorbital region in conjunction with embodiments of a filler manipulator apparatus found in FIG. 1A, FIG. 1B, FIG. 1C, FIG. 2, and FIG. 3; the zygomatic arch region in conjunction with embodiments of a filler manipulator apparatus found in FIG. 1A, FIG. 1B, FIG. 1C, FIG. 2, FIG. 3, and FIG. 4; the mandible region in conjunction with embodiments of a filler manipulator apparatus found in FIG. 4; the buttocks region in conjunction with embodiments of a filler manipulator apparatus found in FIG. 4; the arm region in conjunction with embodiments of a filler manipulator apparatus found in FIG. 4; the leg region in conjunction with embodiments of a filler manipulator apparatus found in FIG. 4; the abdomen region in conjunction with embodiments of a filler manipulator apparatus found in FIG. 4; the foot region in conjunction with embodiments of a filler manipulator apparatus found in FIG. 4; and the vaginal/penile regions in conjunction with embodiments of a filler manipulator apparatus found in FIG. 2, FIG. 3, and FIG. 4. It is also preferred that this embodiment of a filler effector 4 is utilized in rhinoplasty in conjunction with embodiments of a filler manipulator apparatus found in FIG. 1A and FIG. 3 and in lip augmentation (Vermilion border, philtral columns, etc.) in conjunction with embodiments of a filler manipulator apparatus found in FIG. 2.

Figure 5B:
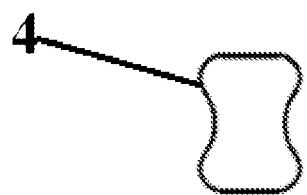
FIG. 5B depicts a side view of an hour glass shaped filler effector according to an embodiment of the current disclosure.

FIG. 5B depicts an embodiment of a filler effector 4. The filler effector 4 is hour glass shaped in appearance, referring to the fact that the diameter of the middle area of the filler effector is smaller than the diameter of the top and bottom areas of the filler effector 4. The filler effector 4 comprises a hollow interior and is hollow to the point where it will comfortably slide onto a tip extension 3 of any embodiment of a filler manipulator apparatus and not drop free off of the tip extension 3. It is noteworthy that the filler effector 4 is allowed to rotate about the tip extension 3 even after the filler effector 4 is securely fastened to the tip extension 3. It is preferred that this embodiment of a filler effector 4 is utilized in the manipulation of the zygomatic arch region in conjunction with embodiments of a filler manipulator apparatus found in FIG. 1A, FIG. 1B, FIG. 1C, FIG. 2, FIG. 3, and FIG. 4; the mandible region in conjunction with embodiments of a filler manipulator apparatus found in FIG. 4; the buttocks region in conjunction with embodiments of a filler manipulator apparatus found in FIG. 4; the arm region in conjunction with embodiments of a filler manipulator apparatus found in FIG. 4; the leg region in conjunction with embodiments of a filler manipulator apparatus found in FIG. 4; the abdomen region in conjunction with embodiments of a filler manipulator apparatus found in FIG. 4; the foot region in conjunction with embodiments of a filler manipulator apparatus found in FIG. 4; and the vaginal/penile regions in conjunction with embodiments of a filler manipulator apparatus found in FIG. 2, FIG. 3, and FIG. 4. It is also preferred that this embodiment of a filler effector 4 is utilized in rhinoplasty in conjunction with embodiments of a filler manipulator apparatus found in FIG. 1A and FIG. 3.

Figure 5C:
FIG. 5C depicts a side view of a filler effector comprising two valleys and a peak on each longitudinal side according to an embodiment of the current disclosure.

FIG. 5C depicts an embodiment of a filler effector 4. The top and bottom edges of the filler effector 4 slope and form two valleys on each side of the filler effector 4. A peak is then formed in the middle that is similar in diameter to the diameter of the top and bottom areas of the filler effector 4. The filler effector 4 further comprises a hollow interior and is hollow to the point where it will comfortably slide onto a tip extension 3 of any embodiment of a filler manipulator apparatus and not drop free off of the tip extension 3. It is noteworthy that the filler effector 4 is allowed to rotate about the tip extension 3 even after the filler effector 4 is securely fastened to the tip extension 3. It is preferred that this embodiment of a filler effector 4 is utilized in the manipulation of the mandible region in conjunction with embodiments of a filler manipulator apparatus found in FIG. 4; the hand region in conjunction with embodiments of a filler manipulator apparatus found in FIG. 1A, FIG. 1B, FIG. 1C, FIG. 2, FIG. 3, and FIG. 4; and the vaginal/penile regions in conjunction with embodiments of a filler manipulator apparatus found in FIG. 2, FIG. 3, and FIG. 4. It is also preferred that this embodiment of a filler effector 4 is utilized in lip augmentation (Vermilion border, philtral columns, etc.) in conjunction with embodiments of a filler manipulator apparatus found in FIG. 2.

Figure 5D:
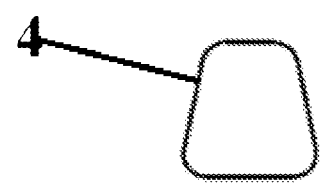
FIG. 5D depicts a side view of a truncated cone shaped filler effector according to an embodiment of the current disclosure.

FIG. 5D depicts an embodiment of a filler effector 4. The filler effector 4 has a shape similar to a truncated cone and comprises a hollow interior. The interior of the filler effector 4 is hollow to the point where it will comfortably slide onto a tip extension 3 of any embodiment of a filler manipulator apparatus and not drop free off of the tip extension 3. It is noteworthy that the filler effector 4 is allowed to rotate about the tip extension 3 even after the filler effector 4 is securely fastened to the tip extension 3. It is preferred that this embodiment of a filler effector 4 is utilized in the manipulation of the zygomatic arch region in conjunction with embodiments of a filler manipulator apparatus found in FIG. 1A, FIG. 1B, FIG. 1C, FIG. 2, FIG. 3, and FIG. 4; the manipulation of the neck region in conjunction with embodiments of a filler manipulator apparatus found in FIG. 4; the hand region in conjunction with embodiments of a filler manipulator apparatus found in FIG. 1A, FIG. 1B, FIG. 1C, FIG. 2, FIG. 3, and FIG. 4; the buttocks region in conjunction with embodiments of a filler manipulator apparatus found in FIG. 4; the arm region in conjunction with embodiments of a filler manipulator apparatus found in FIG. 4; the leg region in conjunction with embodiments of a filler manipulator apparatus found in FIG. 4; the abdomen region in conjunction with embodiments of a filler manipulator apparatus found in FIG. 4; the foot region in conjunction with embodiments of a filler manipulator apparatus found in FIG. 4; and the vaginal/penile regions in conjunction with embodiments of a filler manipulator apparatus found in FIG. 2, FIG. 3, and FIG. 4.

Figure 5E:
FIG. 5E depicts a side view of a truncated ovoid shaped filler effector according to an embodiment of the current disclosure.

FIG. 5E depicts an embodiment of a filler effector 4. The filler effector 4 has a shape similar to a truncated ovoid and comprises a hollow interior. The interior of the filler effector 4 is hollow to the point where it will comfortably slide onto a tip extension 3 of any embodiment of a filler manipulator apparatus and not drop free off of the tip extension 3. It is noteworthy that the filler effector 4 is allowed to rotate about the tip extension 3 even after the filler effector 4 is securely fastened to the tip extension 3. It is preferred that this embodiment of a filler effector 4 is utilized in the manipulation of the periorbital region in conjunction with embodiments of a filler manipulator apparatus found in FIG. 1A, FIG. 1B, FIG. 1C, FIG. 2, and FIG. 3 and the earlobe region in conjunction with embodiments of a filler manipulator apparatus found in FIG. 1A, FIG. 1B, FIG. 1C, FIG. 2, FIG. 3, and FIG. 4.

Figure 5F:
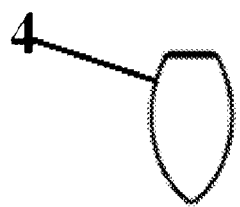
FIG. 5F depicts a side view of a truncated three dimensional almond shaped filler effector according to an embodiment of the current disclosure.

FIG. 5F depicts an embodiment of a filler effector 4. The filler effector 4 has a shape similar to a truncated three dimensional almond and comprises a hollow interior. The interior of the filler effector 4 is hollow to the point where it will comfortably slide onto a tip extension 3 of any embodiment of a filler manipulator apparatus and not drop free off of the tip extension 3. It is noteworthy that the filler effector 4 is allowed to rotate about the tip extension 3 even after the filler effector 4 is securely fastened to the tip extension 3. It is preferred that this embodiment of a filler effector 4 is utilized in the manipulation of the periorbital region in conjunction with embodiments of a filler manipulator apparatus found in FIG. 1A, FIG. 1B, FIG. 1C, FIG. 2, and FIG. 3 and the earlobe region in conjunction with embodiments of a filler manipulator apparatus found in FIG. 1A, FIG. 1B, FIG. 1C, FIG. 2, FIG. 3, and FIG. 4. It is also preferred that this embodiment of a filler effector 4 is utilized in lip augmentation (Vermilion border, philtral columns, etc.) in conjunction with embodiments of a filler manipulator apparatus found in FIG. 2.

Figure 5G:
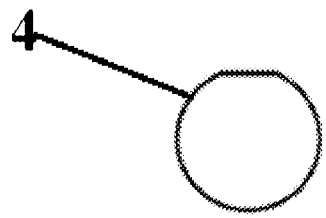
FIG. 5G depicts a side view of a truncated sphere shaped filler effector according to an embodiment of the current disclosure.

FIG. 5G depicts an embodiment of a filler effector 4. The filler effector 4 has a shape similar to a truncated sphere and comprises a hollow interior. The interior of the filler effector 4 is hollow to the point where it will comfortably slide onto a tip extension 3 of any embodiment of a filler manipulator apparatus and not drop free off of the tip extension 3. It is noteworthy that the filler effector 4 is allowed to rotate about the tip extension 3 even after the filler effector 4 is securely fastened to the tip extension 3. It is preferred that this embodiment of a filler effector 4 is utilized in the manipulation of the periorbital region in conjunction with embodiments of a filler manipulator apparatus found in FIG. 1A, FIG. 1B, FIG. 1C, FIG. 2, and FIG. 3; the earlobe region in conjunction with embodiments of a filler manipulator apparatus found in FIG. 1A, FIG. 1B, FIG. 1C, FIG. 2, FIG. 3, and FIG. 4; the buttocks region in conjunction with embodiments of a filler manipulator apparatus found in FIG. 4; the arm region in conjunction with embodiments of a filler manipulator apparatus found in FIG. 4; the leg region in conjunction with embodiments of a filler manipulator apparatus found in FIG. 4; the abdomen region in conjunction with embodiments of a filler manipulator apparatus found in FIG. 4; the foot region in conjunction with embodiments of a filler manipulator apparatus found in FIG. 4; and the vaginal/penile regions in conjunction with embodiments of a filler manipulator apparatus found in FIG. 2, FIG. 3, and FIG. 4.

In another embodiment, a filler effector 4 may be absent of a protuberance. Filler effectors 4 may be connected to a tip extension 3 in a way that does not utilize a protuberance on a filler effector 4. In this case, a protuberance is not needed on a filler effector 4.

In a further embodiment, the filler effectors 4 may be fabricated from a material selected from the group of polymer, composite, metal, metal alloy, and ceramic. In a further embodiment, the filler effectors 4 comprising the above materials may be enveloped in a polymer (such as but not limited to polyurethane, acrylic, polyethylene, silicone, textiles, etc.). The above filler effectors 4 may be included in any of the filler manipulator apparatus embodiments.

In one embodiment, the filler manipulator apparatus and/or filler effectors 4 may be autoclavable (e.g. be made of a material and in a manner that the filler manipulator apparatus and/or the filler effectors 4 may be sterilized in an autoclave).

For the purposes of this disclosure, it is understood that the term "filler manipulator apparatus" may refer to a filler manipulator apparatus including or not including a filler effector 4.

Prior to use, the filler manipulator apparatus is preferably provided in a sterile state within a package or container. The filler effector 4 may be packaged with or separate from the rest of the filler manipulator apparatus. Once free of the packaging, the filler effector 4 may be attached to the tip extension 3 of the filler manipulator apparatus. Once the filler effector 4 is secured to the tip extension 3, the filler manipulator apparatus is ready to be used. The one exception to this is any of the embodiments of the filler manipulator apparatus that comprises an adjustable attachment 6. Before use any of these embodiments, a second portion of the filler manipulator apparatus must be moved to an optimal position before use. The filler effector 4 may then be applied to filler on a body by ideally handling the filler manipulator apparatus using the first elongated section 1, which acts as a handle. This handling of the filler manipulator apparatus will allow for the viable manipulation of filler.

While this disclosure has been particularly shown and described with reference to preferred embodiments thereof and to the accompanying drawings, it will be understood by those skilled in the art that various changes in form and details may be made therein without departing from the spirit of this disclosure. Therefore, the scope of the disclosure is defined not by the detailed description but by the appended claims.

What is claimed is:

1. A filler manipulator apparatus for use in a cosmetic procedure, the filler manipulator apparatus comprising: a first elongated section; a second elongated section, wherein a portion of the second elongated section is connected to a portion of the first elongated section; a tip extension; and a filler effector, wherein a portion of the tip extension is connected to a portion of the second elongated section, and wherein a portion of the tip extension is configured to rotatably support the filler effector; wherein the filler effector is configured to freely rotate about the tip extension when the filler effector is supported by the tip extension and wherein the filler manipulator apparatus is configured to manipulate a previously delivered filler via free rotation of the filler effector about the tip extension, wherein the previously delivered filler is located on or in a body, wherein the filler is for cosmetic use, and wherein the filler effector is configured to be supported in an axially symmetric configuration about said tip extension, wherein the tip extension and filler effector are configured to securely fasten via at least one of:
i) a circumferential protuberance on the tip extension or filler effector and a corresponding circumferential groove on the filler effector or tip extension, respectively, wherein the circumferential protuberance is configured to be received within said circumferential groove for interlocking, ii) a snap ring on said tip extension and/or filler effector,
iii) a circumferential protuberance on both the tip extension and filler effector, or
iv) combinations thereof.

2. The filler manipulator apparatus of claim 1 wherein the first elongated section comprises grooves.

3. The filler manipulator apparatus of claim 1 wherein the first elongated section is larger in diameter than the second elongated section and the tip extension.

4. The filler manipulator apparatus of claim 1 wherein the first elongated section comprises an exterior high friction layer.

5. The filler manipulator apparatus of claim 1 wherein the second elongated section comprises a ball and socket joint.

6. The filler manipulator apparatus of claim 1 wherein the second elongated section comprises at least one bend in the structure of the second elongated section.

7. The filler manipulator apparatus of claim 1 wherein the second elongated section comprises more than one bend in the structure of the second elongated section.

8. The filler manipulator apparatus of claim 1 wherein the tip extension comprises the circumferential protuberance.

9. The filler manipulator apparatus of claim 1 wherein the tip extension section comprises the circumferential groove.

10. The filler manipulator apparatus of claim 1 wherein the tip extension comprises the snap ring.

11. The filler manipulator apparatus of claim 1, the filler effector, wherein the filler effector comprises the circumferential protuberance.

12. The filler manipulator apparatus of claim 1, wherein a portion of the filler effector is enveloped in a polymer.

13. The filler manipulator apparatus of claim 1 wherein a first portion of the filler manipulator apparatus is adjustably attached to a second portion of the filler manipulator apparatus using an adjustable attachment.

14. The filler manipulator apparatus of claim 1, wherein the filler effector is substantially cylindrical.

15. The filler manipulator apparatus of claim 1, wherein the filler effector is substantially an hour glass shape.

16. The filler manipulator apparatus of claim 1, wherein the filler effector is substantially shaped to have a slope and two valleys on each side of the filler effector.

17. The filler manipulator apparatus of claim 1, wherein the filler effector is substantially a truncated cone.

18. The filler manipulator apparatus of claim 1, wherein the filler effector is substantially a truncated ovoid.

19. A filler manipulator system for use in a cosmetic procedure, the filler manipulator system comprising:
a handle;
a tip extension coupled to or integral with the handle, and a filler effector, wherein the tip extension is configured to rotatably and securely support the filler effector for free axial rotation of the filler effector about the tip extension,
wherein the filler manipulator system is configured to manipulate a previously delivered filler located on or in a body via said free axial rotation of the filler effector with respect to the tip extension, and wherein the filler is for cosmetic use,
wherein the filler effector is configured to be supported in an axially symmetric configuration about said tip extension, wherein the tip extension and filler effector are configured to securely fasten via at least one of:
i) a circumferential protuberance on the tip extension or filler effector and a corresponding circumferential groove on the filler effector or tip extension, respectively, wherein the circumferential protuberance is configured to be received within said circumferential groove for interlocking,
ii) a snap ring on said tip extension and/or filler effector,
iii) a circumferential protuberance on both the tip extension and filler effector, or
iv) combinations thereof.

* * * * *